(12) United States Patent
Takahashi et al.

(10) Patent No.: US 10,806,562 B2
(45) Date of Patent: Oct. 20, 2020

(54) STENT GRAFT

(71) Applicant: Asahi Kasei Kabushiki Kaisha, Tokyo (JP)

(72) Inventors: Tetsuko Takahashi, Tokyo (JP); Junichi Kojima, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 55 days.

(21) Appl. No.: 15/558,269

(22) PCT Filed: Mar. 31, 2016

(86) PCT No.: PCT/JP2016/060734
§ 371 (c)(1),
(2) Date: Sep. 14, 2017

(87) PCT Pub. No.: WO2016/159264
PCT Pub. Date: Oct. 6, 2016

(65) Prior Publication Data
US 2018/0078357 A1    Mar. 22, 2018

(30) Foreign Application Priority Data

Apr. 3, 2015  (JP) ................................. 2015-077074

(51) Int. Cl.
*A61F 2/07* (2013.01)
*D03D 3/02* (2006.01)
(Continued)

(52) U.S. Cl.
CPC ................ *A61F 2/07* (2013.01); *A61L 17/10* (2013.01); *A61L 17/105* (2013.01); *A61L 31/06* (2013.01);
(Continued)

(58) Field of Classification Search
CPC .................. A61F 2/07; A61F 2002/072; A61F 2002/075; A61F 2002/077;
(Continued)

(56) References Cited

U.S. PATENT DOCUMENTS 5,102,419 A    4/1992  Gertzman et al.
5,147,382 A *  9/1992  Gertzman ............... A61L 17/04
                                                606/228
(Continued)

FOREIGN PATENT DOCUMENTS

EP    0174180 A1    3/1986
EP    1543798 A2    6/2005
(Continued)

OTHER PUBLICATIONS

International Preliminary Report on Patentability issued in corresponding International Patent Application No. PCT/JP2016/060734 dated Oct. 12, 2017.
(Continued)

*Primary Examiner* — Melanie R Tyson
(74) *Attorney, Agent, or Firm* — Morgan, Lewis & Bockius LLP

(57) ABSTRACT

A low-profile stent graft has a Type-III endoleak suppression effect, avoiding the problem with a stent graft which uses an extra-thin graft incurring enlarged needle holes or needle hole parts in a suture part. The stent graft has a proximate end, a distal end, and a lumen which is positioned between the proximate end and the distal end. The stent graft is formed by coupling a cylindrical graft to a stent with a suture. The cylindrical graft is formed from a fabric having a thickness of 10-90 μm. The elastic modulus of the suture is 40 cN/dtex or less.

23 Claims, 6 Drawing Sheets

(51) Int. Cl.
*D03D 1/00* (2006.01)
*D03D 15/00* (2006.01)
*A61L 17/10* (2006.01)
*A61L 31/06* (2006.01)

(52) U.S. Cl.
CPC ............... *D03D 1/00* (2013.01); *D03D 3/02* (2013.01); *D03D 15/00* (2013.01); *A61F 2002/075* (2013.01); *A61F 2220/0075* (2013.01); *D10B 2331/04* (2013.01); *D10B 2509/06* (2013.01)

(58) Field of Classification Search
CPC ....... A61F 2220/0075; A61B 17/06166; A61B 2017/0618; A61B 2017/00663; A61L 17/00; A61L 17/04; A61L 17/06; A61L 17/10; A61L 17/105; A10B 2509/04; D10B 2509/06; D02G 3/448
See application file for complete search history.

(56) References Cited

U.S. PATENT DOCUMENTS

| | | | |
|---|---|---|---|
| 6,458,148 B1 | 10/2002 | Dauner et al. | |
| 2009/0048628 A1* | 2/2009 | Marissen | A61B 17/06166 606/231 |
| 2010/0274282 A1 | 10/2010 | Olson | |
| 2013/0041452 A1* | 2/2013 | Fujita | D04B 21/16 623/1.13 |
| 2013/0205979 A1* | 8/2013 | Nelis | D02G 3/448 87/7 |
| 2014/0199362 A1* | 7/2014 | Clay | A61B 17/06166 424/423 |
| 2015/0247269 A1 | 9/2015 | Fukushima et al. | |
| 2015/0366653 A1 | 12/2015 | Noishiki | |
| 2016/0135944 A1 | 5/2016 | Saito et al. | |
| 2016/0184488 A1 | 6/2016 | Toyoda et al. | |

FOREIGN PATENT DOCUMENTS

| | | |
|---|---|---|
| EP | 2826894 A1 | 1/2015 |
| JP | S55-101266 A | 8/1980 |
| JP | S61-071058 A | 4/1986 |
| JP | H04-089065 A | 3/1992 |
| JP | 2000-225198 A | 8/2000 |
| JP | 2000-271210 A | 10/2000 |
| JP | 2010-255175 A | 11/2010 |
| WO | 2014/050962 A1 | 4/2014 |
| WO | 2014/132454 A1 | 9/2014 |
| WO | 2015/005105 A1 | 1/2015 |
| WO | 2015/037671 A1 | 3/2015 |

OTHER PUBLICATIONS

International Search Report issued in corresponding International Patent Application No. PCT/JP2016/060734 dated Jul. 5, 2016.
Written Opinion issued in corresponding International Patent Application No. PCT/JP2016/060734 dated Jul. 5, 2016.
Supplementary European Search Report issued in corresponding European Patent Application No. 16773144.7 dated Mar. 8, 2018.
Office Action issued in corresponding European Patent Application No. 16773144.7 dated Mar. 27, 2018.

* cited by examiner

NORMAL EYE TYPE

SPRING EYE TYPE

THREADED TYPE

STENT GRAFT

BACKGROUND OF THE INVENTION

Field of the Invention

The present invention relates to a stent graft comprising a stent and a tubular fabric (hereinafter, also referred to as a graft).

Description of the Related Art

Stent grafts are medical devices for use in the treatment of thoracic or abdominal aortic aneurysm and are in the form of an artificial blood vessel fitted with a tubular fabric, for example, in a spring-like metal known as a stent. The intravascular treatment of aortic aneurysm using the stent graft is, for example, a method of treatment in which: the artery at the base of the foot is incised; a catheter having the stent graft compressively inserted therein (stent graft device) is introduced through the incision and transferred to the affected area of aneurysm using a guide wire; and the stent graft is opened from the catheter and indwelled at the affected area, whereby blood flow into the aneurysm is blocked and burst of the aneurysm is prevented. Unlike artificial blood vessel replacement, which is a conventional method for treating aortic aneurysm, this treatment method does not involve thoracotomy or laparotomy. Therefore, in recent years, its application has been rapidly increasing because physical burdens or economical burdens ascribable to long-term hospitalization on patients are reduced.

However, most of currently commercially available stent graft devices have a catheter outer diameter exceeding 18 Fr (French) (3 Fr is 1 mm; thus 18 Fr corresponds to a diameter of 6 mm). In many cases, females and Asians have less than 6 mm diameters of iliac arteries serving as routes for catheterization. In this case, treatment using stent grafts is rarely selectable. Also, aneurysm patients may have preexisting conditions such as diabetes mellitus, and their blood vessels are often fragile and calcified. Therefore, the risk of vascular damage is increased during access to the affected areas even if the diameters of blood vessels are larger than the diameters of catheters.

Thus, the need for reducing the diameters of stent graft devices (low profile stent graft devices) has been rapidly growing in recent years in order to widen the range of applications to patients or reduce the risk of vascular damage. For the low profile stent graft devices, it is effective to reduce the wall thickness of a graft that occupies a large proportion of a catheter cross section area when a stent graft is compressively inserted in a catheter. The inventors of the present application have proposed a tubular seamless woven fabric made of a superfine polyester fiber that possesses both thinness and practical performance (International Publication No. WO2013/137263).

However, the reduction in the wall thickness of a graft faces challenges as described below.

Stent grafts are produced by a method which involves sewing a stent to a graft using a surgical suture needle and suture thread under tension on the order of typically 50 to 100 g. Needle holes are easily opened in grafts having a small wall thickness. In addition, stent grafts are placed under beating with constant pressure (blood pressure) over a long period of several years to several tens of years after indwelling within blood vessels. Needle holes at suture sites of stents and grafts may be gradually enlarged. Such enlargement of needle holes has also been observed in prolonged durability tests (based on ISO7198) on stent grafts using very thin grafts.

Both of such "easy opening of needle holes" and "enlargement of needle holes" lead to endoleak to aneurysm. Hereinafter, endoleak originating from needle holes at graft suture sites is also referred to as "type III endoleak".

As measures against the type III endoleak of stent grafts, there have been proposed a method for filling needle holes or enlarged needle holes by attaching film-coated grommets to graft suture sites (see U.S. Patent Application Publication No. 2009/149939), and a method for preventing the enlargement of damaged sections in grafts having a small wall thickness by weaving the grafts to have ripstop texture (see JP-A-2011-229713).

However, in the stent graft described in U.S. Patent Application Publication No. 2009/149939, the wall thickness of the graft is increased by the thicknesses of grommets because a large number of grommets having a structure with two metal rings that sandwich the graft are attached throughout the graft. Furthermore, the stent graft cannot be folded small because the grommets interfere with each other when the stent graft is compressively inserted in a catheter. Thus, this stent graft cannot meet low profiles of stent graft devices.

In the method of JP-A-2011-229713, only sections where thick yarns constituting ripstop texture are present are effective for preventing needle hole enlargement. Thus, this method cannot ensure the effect of preventing needle hole enlargement for all suture sites.

As mentioned above, any realistic solution to the problems of needle holes at suture sites of grafts and stents or enlargement of needle holes has not yet been found. Furthermore, any solution to these problems in the case of using very thin grafts that allow stent graft devices to have a low profile has not been even proposed so far.

Under the circumstances, an object of the present invention is to provide a stent graft that is free from the problems of needle holes at suture sites in stent grafts using very thin grafts and enlargement of needle holes, and is effective for suppressing type III endoleak.

SUMMARY OF THE INVENTION

The present inventors have conducted diligent studies and experiments to attain the object and consequently completed the present invention by finding that the physical properties of a suture thread for fixing a stent to a graft, particularly, the modulus of elasticity of the suture thread, strongly correlates with needle holes at suture sites associated with very thin grafts and enlargement of needle holes.

Specifically, the present invention is as described below.

[1] A stent graft comprising a proximal end, distal end, and a lumen disposed between the proximal end and the distal end, wherein the stent graft comprises a tubular graft and a stent joined together with a suture thread(s), the tubular graft is a woven fabric having a thickness of 10 μm or larger and 90 μm or smaller, and the suture thread has a modulus of elasticity of 40 cN/dtex or less.

[2] The stent graft according to [1], wherein the suture thread has a fiber diameter of 350 μm or smaller.

[3] The stent graft according to [1] or [2], wherein the suture thread is a multifilament made of at least one selected from the group consisting of polyester, polyamide, polyolefin, polytetrafluoroethylene, and silk.

[4] The stent graft according to any of [1] to [3], wherein the suture thread is in a braid form in which three or more fiber bundles (yarns) each comprising a plurality of filaments are interlaced, and the braid has a braiding angle of 8° or larger and 30° or smaller and a braiding density of 12 counts/cm or higher and 45 counts/cm or lower.

[5] The stent graft according to [4], wherein the fiber bundles are textured yarns having a porosity of 4 to 70%.

[6] The stent graft according to [4] or [5], wherein the fiber bundles are made of polyester and have a total fineness of 30 dtex or more and 200 dtex or less and a single filament fineness of 1.0 dtex or less.

[7] The stent graft according to any of [1] to [6], wherein the graft is a woven fabric composed of multifilaments made of at least one selected from the group consisting of polyester, polyamide, polyolefin, polytetrafluoroethylene, and silk.

[8] The stent graft according to [7], wherein the graft is a woven fabric composed of polyester.

[9] The stent graft according to [7], wherein the graft is a seamless woven fabric composed of a polyester fiber containing 90 wt % or more of polyethylene terephthalate with respect to the graft weight, and the polyester fiber has a total fineness of 7 dtex or more and 120 dtex or less and a single filament fineness of 1.0 dtex or less.

[10] The stent graft according to any of [1] to [9], wherein when the suture thread inserted through the graft is pulled with a load of 60 g, a needle hole area of 0.025 mm$^2$ or smaller is generated in the graft.

[11] A stent graft device comprising the stent graft according to any of [1] to [10].

The stent graft of the present invention can attain a low profile, which can therefore reduce the physical and economical burdens on patients in such a way as to shorten the inpatient periods, and can also reduce risks such as vascular wall damage. Furthermore, the stent graft of the present invention can widen the range of applications even to cases that have hitherto been excluded as targets of intravascular treatment, such as females and Asians that have narrower arteries. In addition, the stent graft of the present invention minimizes needle holes at suture sites and suppresses needle hole enlargement under a long-term beating environment. Therefore, the stent graft of the present invention can reduce the risk of type III endoleak.

DETAILED DESCRIPTION OF THE PREFERRED EMBODIMENTS

Figure 1:
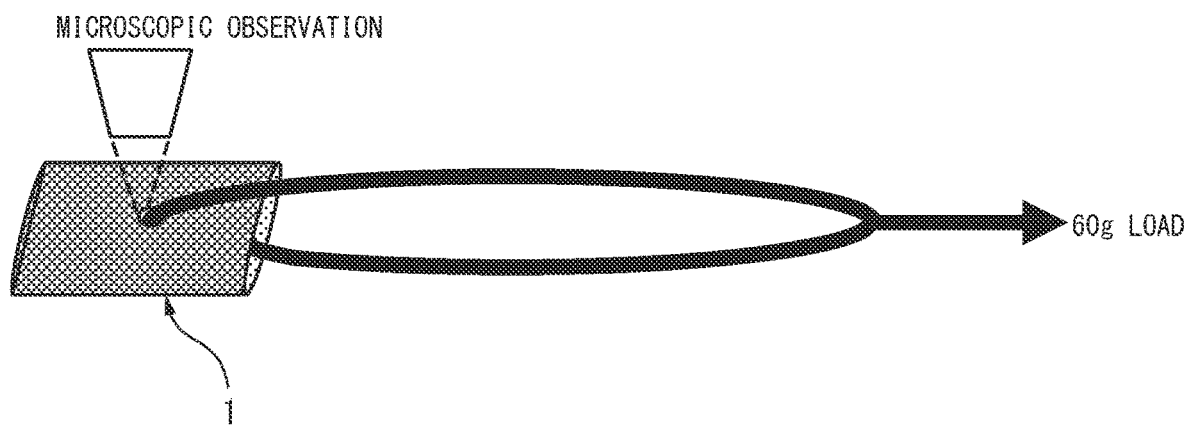
FIG. 1 is a diagram illustrating a method for measuring a needle hole size.

Hereinafter, the embodiments of the present invention will be described in detail.

The graft constituting the stent graft of the present embodiment is a tubular fabric having a thickness of 10 μm or larger and 90 μm or smaller.

The thickness of the graft is defined as the average of thicknesses measured with a thickness gauge at a total of 12 positions involving four roughly equally spaced positions in the circumferential direction of the graft measured three times in the length direction (10 cm to 30 cm). A graft having a thickness exceeding 90 μm is not able to pass through a 6 mm diameter hole, when prepared into a tubular fabric with an outer diameter of 50 mm, for example. On the other hand, a fabric having a thickness smaller than 10 μm presents problems associated with practical performance, such as deterioration in durability and endoleak. The thickness of the graft is preferably 15 μm or larger and 85 μm or smaller, more preferably 30 μm or larger and 80 μm or smaller, from the viewpoint of achieving both of a low profile stent graft and excellent practical performance.

The graft constituting the stent graft of the present embodiment may be a tubular seamless woven fabric or may have a structure of a plane woven fabric sewn in a tubular form. A tubular seamless woven fabric is more preferred because the resulting stent graft can be folded thinner. The fiber constituting the graft is preferably a monofilament or multifilament made of at least one selected from the group consisting of a polyester fiber, a polyamide fiber, a polyethylene fiber, a polytetrafluoroethylene (hereinafter, abbreviated to PTFE) fiber, and silk. A woven fabric of a polyester fiber or a PTFE fiber heretofore used in artificial blood vessels or stent grafts and confirmed to be safe is more preferred because of coming in direct contact with blood. A polyester fiber is most preferred from the viewpoint of the burst strength of the graft. In this context, the polyester substantially refers to polyethylene terephthalate (hereinafter, abbreviated to PET), but may contain or be coated with a component other than PET as long as the desired effects are exerted and as long as biological safety is not inhibited.

For the polyester fiber constituting the graft, it is preferred that a superfine polyester fiber that is a multifilament with a filament number of 2 or more and has total fineness (the product of fineness per monofilament (single filament fineness) and the filament number) of 7 dtex or more and 120 dtex or less and single filament fineness of 1.0 dtex or less should be disposed in warp yarn and/or weft yarn of the graft, from the viewpoint of preventing endoleak from a proximal site or a distal site caused by wrinkles of the graft (type I endoleak), endoleak from needle holes or damaged sections in the graft (type III endoleak), and endoleak from graft wall face (type IV endoleak). To cope with the type I endoleak, the graft having this configuration in which a superfine polyester fiber is disposed in warp yarn and/or weft yarn resists folding wrinkles. Thus, the endoleak from a proximal site or a distal site is unlikely to occur because there is no space for entry of blood between the vascular wall and the stent graft when the stent graft is opened at the affected area. To cope with the type III endoleak, many superfine filaments constituting the graft cover needle holes after needle puncture to fill the holes. To cope with the type IV endoleak, a layer of many filaments inhibits blood flow toward graft wall face and prevents the endoleak. The polyester fiber constituting the warp yarn and/or the weft yarn of the graft has total fineness of more preferably 10 dtex or more and 110 dtex or less, further preferably 15 dtex or more and 100 dtex or less, and single filament fineness of more preferably 0.5 dtex or less, from the viewpoint that the graft possesses both thinness and resistance to endoleak. The lower limit of the single filament fineness is not particularly limited and is preferably 0.01 dtex or more, more preferably 0.03 dtex or more, from the viewpoint of the prolonged durability of the graft.

The woven structure of the graft constituting the stent graft of the present embodiment is not particularly limited and is preferably a plain weave structure or a twill weave structure from the viewpoint of graft thinness and endoleak prevention. The cover factors of the warp yarn and the weft yarn of the graft are both preferably 800 or more, and the sum of the cover factors of the warp yarn and the weft yarn is preferably 1600 to 2400, from the viewpoint of endoleak prevention. The cover factors are calculated according to the following expressions using woven densities measured on the basis of JIS L 1096 (2010) 8.6.1:

Warp yarn cover factor=(Warp yarn total fineness: dtex)$^{1/2}$×(Warp yarn woven density: the number of warps/2.54 cm)

Weft yarn cover factor=(Weft yarn total fineness: dtex)$^{1/2}$×(Weft yarn woven density: the number of wefts/2.54 cm)

The modulus of elasticity of the suture thread that joins the graft and a stent together in the stent graft of the present embodiment is 40 cN/dtex or less. The modulus of elasticity of the suture thread strongly correlates with a needle hole size at suture sites of stents and grafts and an event of the needle hole enlargement of suture sites over time. In this context, the needle hole size is a value obtained by inserting the suture thread through the tubular graft mounted to a fixture with a width adjustable according to the diameter of graft 1 as shown in FIG. 1, and measuring the area of the needle hole under a microscope when the suture thread is pulled with a load of 60 g. In this context, the needle hole size is 0.025 mm$^2$ or smaller when a graft having a general thickness (graft that has a plain weave structure where a polyester multifilament having a filament fiber diameter of approximately 20 μm is disposed in warp yarn and weft yarn, and has a wall thickness of 100 to 200 μm and a water permeability (based on ISO7198; index for endoleak) of 500 cc/min/cm$^2$ or less) is evaluated by the method using a general polyester braid suture thread (thickness: 200 to 300 μm) for use in assembly of stent grafts. Therefore, an index for the needle hole size is 0.025 mm$^2$ or smaller.

In the present specification, the modulus of elasticity of the suture thread that joins the graft and, a stent together is an initial modulus of elasticity calculated from a load for 1% tensile elongation and a load for 2% elongation using data on load (also called stress) vs. elongation (also called strain) during pulling of the suture thread measured according to JIS-L-1013. A suture thread having a larger modulus of elasticity tends to increase the needle hole size in very thin grafts. Surprisingly, if the modulus of elasticity exceeds 40 cN/dtex, the needle hole size is drastically increased to exceed 0.025 cm$^2$. The reason why the needle hole size depends on the modulus of elasticity of the suture thread and the reason why this event has a critical point are not clear. If the suture thread has a high modulus of elasticity, suture load is directly applied to graft texture to enlarge needle holes. By contrast, the suture thread having a small modulus of elasticity presumably absorbs suture load and does not act on the needle hole enlargement of the graft.

For the same reason as above, the modulus of elasticity of the suture thread that joins the graft and a stent together influences an effect of preventing the enlargement of needle holes at suture sites in a long period and under a beating environment within a blood vessel. Specifically, the stent and the graft are physically joined together with the suture thread. Since the stent and the graft differ totally in solid state structure, their motions do not completely resonate with each other under a beating environment within a blood vessel. Force generated by the difference between their motions is directly applied to suture sites in the graft. The suture thread having a small modulus of elasticity absorbs the force applied to suture sites by beating. As a result, the stent graft can maintain performance as an artificial blood vessel without enlarging needle holes at the suture sites even under a beating environment and without causing endoleak over a long period. The modulus of elasticity of the suture thread is preferably 35 cN/dtex or less, more preferably 30 cN/dtex or less, from the viewpoint of the needle hole size and the prevention of needle hole enlargement over a long period. The suture thread having a small modulus of elasticity is elongated by force generated by vasomotion and impairs the integrity between the graft and the stent, resulting in degradation attributed to graft surface abrasion. Therefore, the lower limit of the modulus of elasticity of the suture thread is preferably 1 cN/dtex, more preferably 2 cN/dtex.

In a preferred embodiment, the very thin graft used in the stent graft of the present embodiment is composed of a superfine fiber. The superfine fiber has small single filament fineness and therefore increases the risk of degradation attributed to abrasion on the graft surface due to the friction generated between the stent and the very thin graft in conjunction with vasomotion, as compared with use of a regular thickness fiber. Thus, the suture thread constituting the stent graft of the present embodiment preferably has an elongation percentage of 0.2% or more and 2.0% or less under a load of 60 g from the viewpoint of suppressing degradation attributed to graft surface abrasion. A suture thread having an elongation percentage exceeding 2.0% is elongated by force generated by vasomotion and impairs the integrity between the graft and the stent, resulting in degradation attributed to graft surface abrasion. On the other hand, if the elongation percentage of the suture thread is smaller than 0.2%, tension on the suture thread is applied to the graft to make large needle holes. The elongation percentage of the suture thread constituting the stent graft of the present embodiment is more preferably 0.3% or more and 1.8% or less, further preferably 0.4% or more and 1.5% or less.

The thickness (fiber diameter) of the suture thread is preferably 350 μm or smaller. If the fiber diameter of the suture thread exceeds 350 μm, the proportion of the suture thread to a catheter cross section area is high during compression of the stent graft. This inhibits a low profile of a stent graft device. Therefore, the fiber diameter of the suture thread is preferably 350 μm or smaller, more preferably 320 μm or smaller, further preferably 300 μm or smaller.

The material for the suture thread constituting the stent graft of the present embodiment is not particularly limited and is preferably selected from the group consisting of a polyester fiber (e.g., PET and polybutylene terephthalate), a polyamide fiber (e.g., nylon 66), a polyolefin fiber (e.g., polyethylene and polypropylene), a polytetrafluoroethylene fiber, and silk, from the viewpoint of biocompatibility. Also, the material is preferably selected from the group consisting of a polyester fiber, a polyamide fiber, and a polytetrafluoroethylene fiber, from the viewpoint of controlling the modulus of elasticity of the suture thread to within the range specified by the present invention by way of the unique modulus of elasticity of the material.

The suture thread of the present embodiment may be a monofilament or may be a multifilament as long as the elongation property described above is satisfied. Since the monofilament has a large bending rate, the monofilament may impair the integrity between the graft and the stent or easily become untied. Therefore, a multifilament is preferred, and a multifilament having a single filament fineness of 1 dtex or less is more preferred. This increases the flexibility of the suture thread and improves the integrity between the stent and the graft, while obstacles to insertion in a catheter rarely arise.

A plurality of filaments constituting the fiber bundle may be textured in the porosity range of 4% or more and 70% or less, more preferably 4% or more and 50% or less. Fibroblasts enter moderate spaces formed between the filaments of the suture thread, and are organized, thereby filling needle holes at suture sites while helping to exhibit an effect of reinforcing the suture sites in living tissues. In addition, the modulus of elasticity of the suture thread can also be controlled to within the range of the present invention. The multifilament suture thread is preferably in a braid form in which three or more fiber bundles (yarns) each comprising a plurality of filaments are interlaced. The suture thread having a braid structure preferably has a braiding angle (angle of a fiber bundle spirally oriented with respect to the axial direction of the braid) of 8° or larger and a braiding density (counts per unit length) of 12 counts/cm or higher. When the suture thread is designed such that the braiding angle and the braiding density fall within these ranges, the modulus of elasticity of the suture thread can be controlled to the range specified by the present invention. Also, the suture thread designed such that the braiding angle and the braiding density fall within the range described above is easily flattened under stress in the cross sectional direction. Therefore, when the stent graft is compressively inserted in a catheter, the proportion of the suture thread to a catheter cross section area is decreased. This can contribute to low profile stent graft devices.

On the other hand, the basic requirements for the performance of the suture thread that joins the stent and the graft together are that: the knot of the suture thread is unlikely to become untied; and the strength for fixing the stent and the graft together is not gradually reduced. When the braiding angle and the braiding density are equal to or higher than the lower limits described above, the knot of the suture thread is difficult to untie. If the braid suture thread has a braiding angle exceeding 30° and a braiding density exceeding 45 counts/cm, stress relaxation caused by structurally formed spaces loosens the knot or reduces over time the strength for fixing the stent and the graft together. Thus, the integrity between the stent and the graft is impaired. If the braiding angle and the braiding density of the braid suture thread exceed the upper limits described above, the fiber diameter of the suture thread is increased so that obstacles to insertion in a catheter arise. Thus, the range of the braiding angle of the suture thread constituting the stent graft of the present embodiment is preferably 8° or larger and 30° or smaller, more preferably 10° or larger and 28° or smaller, further preferably 15° or larger and 25° or smaller. Likewise, the range of the braiding density of the suture thread constituting the stent graft of the present embodiment is preferably 12 counts/cm or higher and 45 counts/cm or lower, more preferably 15 counts/cm or higher and 42 counts/cm or lower, further preferably 15 counts/cm or higher and 40 counts/cm or lower.

As mentioned above, various characteristics of the suture thread contributing to solution to the problems of stent grafts are the physical properties of the suture thread in a finally sterilized sewn stent graft. Methods for sterilizing medical equipment include heat sterilization methods such as autoclave sterilization using high pressure steam and dry heat sterilization using dry hot air, radiation sterilization methods using γ-ray or electronic beam, and gas sterilization methods using ethylene oxide gas or low temperature gas plasma of hydrogen peroxide. Sterilization methods or treatment conditions for medical equipment are selected depending on the type and properties of matter to be sterilized, the state of storage in a container, etc. Similarly, a sterilization method or treatment conditions for the stent graft are determined according to the properties of the stent, the graft, and other members, etc. Various physical properties described above, such as the modulus of elasticity, the braiding angle, and the braiding density of the suture thread, vary depending on the production histories of the suture thread, the method for finally sterilizing the stent graft, and its treatment conditions. For example, when the stent graft is produced, using an unsterilized suture thread composed of highly molecularly oriented polyester fiber bundles, and sterilized with dry hot air of 160 to 200° C., the modulus of elasticity of the suture thread, even if exceeding 40 cN/dtex before sterilization, may become 40 cN/dtex or less after the sterilization due to the thermal relaxation of the orientation. On the other hand, in the case of using the same polyester suture thread as above and adopting ethylene oxide gas sterilization, the treatment temperature is approximately 60° C., which is lower than the glass transition temperature of the polyester fiber (80 to 90° C.). Therefore, the modulus of elasticity of the suture thread does not become 40 cN/dtex or less after the sterilization. For attaining the object of the present invention (prevention of endoleak from needle holes after stent graft indwelling, and prevention of needle hole enlargement), the important thing is the physical properties of the suture thread in the finally sterilized sewn stent graft, not the physical properties of the suture thread used in the production of the stent graft.

Figure 2:
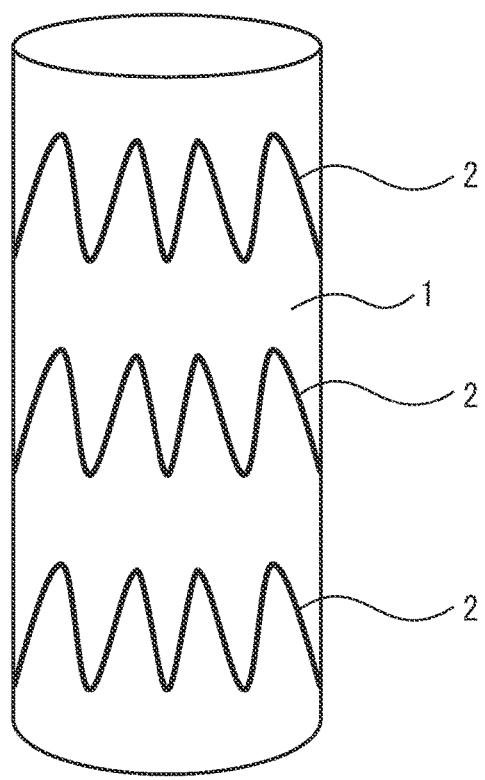
FIG. 2 is a diagram showing the basic skeleton of a stent graft.
Figure 3:
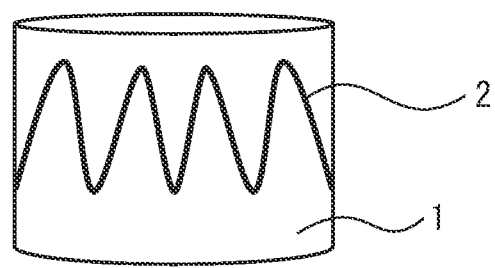
FIG. 3 is a diagram showing one unit structure of the stent graft.
Figure 4:
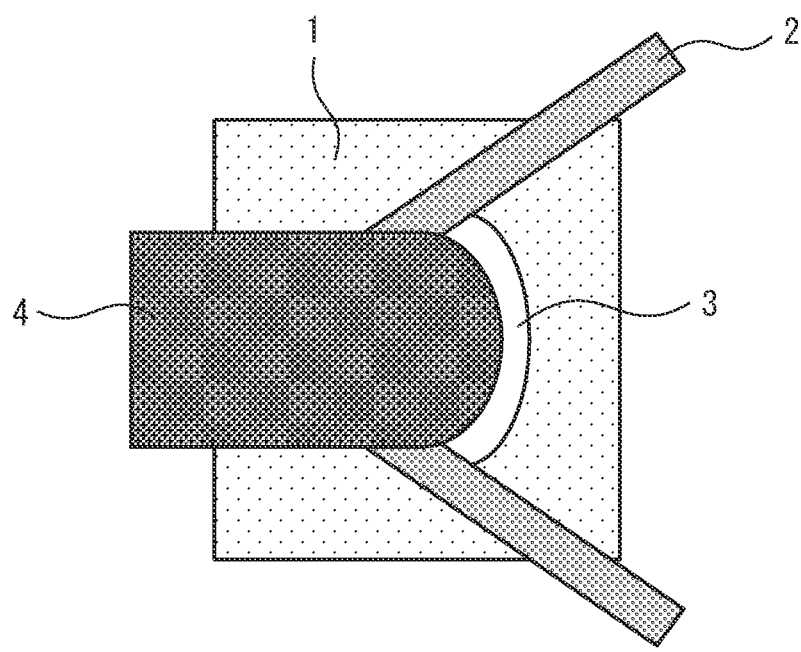
FIG. 4 is a diagram showing a needle hole model that is made during stent graft suture.

The length, diameter, and form of the stent graft to be applied differ depending on an affected area and the diameters and structures of blood vessels near the affected area. In a basic skeleton, as shown in FIG. 2, stent rings 2 are deployed on the circumference of graft 1. The stent graft of the present embodiment comprising the stent and the graft with a thickness of 10 μm to 90 μm joined together with the suture thread having a modulus of elasticity of 40 cN/dtex or less has 10 or less, preferably 6 or less, more preferably 5 or less needle holes larger than 0.025 cm² per structural unit shown in FIG. 3 and has a water permeability (defined according to ISO7198:8.2.3) of 500 cc/min/cm² or less, preferably 300 cc/min/cm² or less, per structural unit, irrespective of the stent shape or the number of stitches. The needle hole defined herein is, as shown in FIG. 4, needle hole 3 that permits penetration of suture thread 4, and its area measured by observing the stent graft on a structural unit basis in the circumferential direction under a microscope.

The method for producing the stent graft of the present embodiment is not particularly limited. Hereinafter, one embodiment thereof will be described.

The stent graft of the present embodiment is produced by joining together a graft having a thickness of 10 μm to 90 μm and a stent (spring-like metal) serving as an inflatable member by sewing using a suture thread. Since the stent graft is sterilized with ethylene oxide gas, γ-ray, high pressure steam, or the like in a final step, the suture thread used in this process is preferably a suture thread that satisfies the requirements of the modulus of elasticity specified by the present invention after the sterilization. More preferably, a sterilized suture thread found to have a modulus of elasticity of 40 cN/dtex or less is easily selectable. The stent used may be made of a self-inflating material using a shape memory alloy, a superelastic metal, or a synthetic polymer material, or a type that expands with a balloon may be applied to the stent. The inflatable member may have any design of a conventional technique.

The modulus of elasticity of the suture thread of the present invention is defined as a post-sterilization value in a final product. Therefore, the suture thread for use in the production of the stent graft can be selected such that the post-sterilization modulus of elasticity is controlled to 40 cN/dtex or less. The thickness of the graft of the present embodiment is as small as 10 μm to 90 μm. Thus, large needle holes may be opened in the graft, depending on how to apply tension to the suture thread during suture. Therefore, it is preferred to use an already sterilized suture thread having a modulus of elasticity of 40 cN/dtex or less. Use of such a suture thread widens the allowable range of tension applied to the suture thread, and reduces the number of needle holes larger than 0.025 cm$^2$ to 10 or less per structural unit of the stent graft, also leading to improvement in production efficiency by shortening of a suture time, rise in yield, etc. The suture thread, for use in the production of the stent graft of the present embodiment preferably has a braid structure with a braiding angle (angle of a fiber bundle spirally oriented with respect to the axial direction of the braid) of 8° or larger and 30° or smaller and a braiding density (counts per unit length) of 12 counts/cm or higher and 45 counts/cm or lower. Use of the suture thread having a braid structure designed such that the braiding angle and the braiding density fall within the ranges described above widens the allowable range of tension applied to the suture thread. In addition, the knot of the suture thread is difficult to untie, as mentioned above. This facilitates the inevitable operation of tying the knot of the suture thread in the suture process, leading to improvement in production efficiency.

The shape of the suture needle for use in the suture of the stent and the graft includes a cutting needle and a round needle. Since the cutting needle has a point processed into a knife shape, the cutting needle might break the fiber constituting the very thin graft during suture of the graft constituting the stent graft of the present embodiment so that holes are enlarged over time after indwelling. Therefore, it is preferred to use a suture needle having a round needle shape. For preventing needle holes larger than 0.025 cm$^2$ from being opened in the very thin graft during suture, it is preferred that the thickness of the suture needle for the suture of the very thin graft and the stent constituting the stent graft of the present embodiment should not exceed 700 μm at its root, which is thickest.

Figure 5:
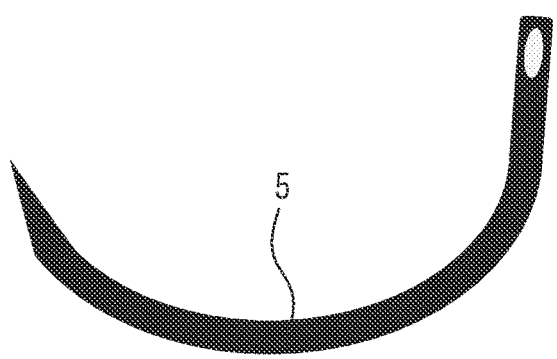
FIG. 5 is a diagram showing the shape of a suture thread fitting site (root) of a suture needle.
Figure 5:
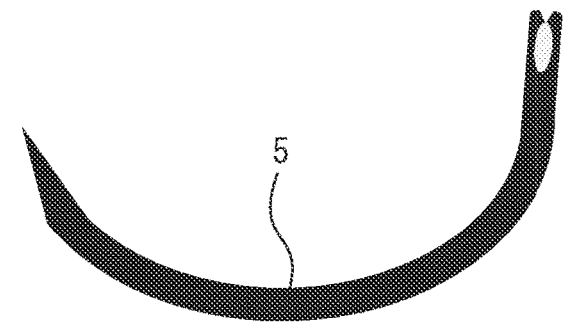
Figure 5:
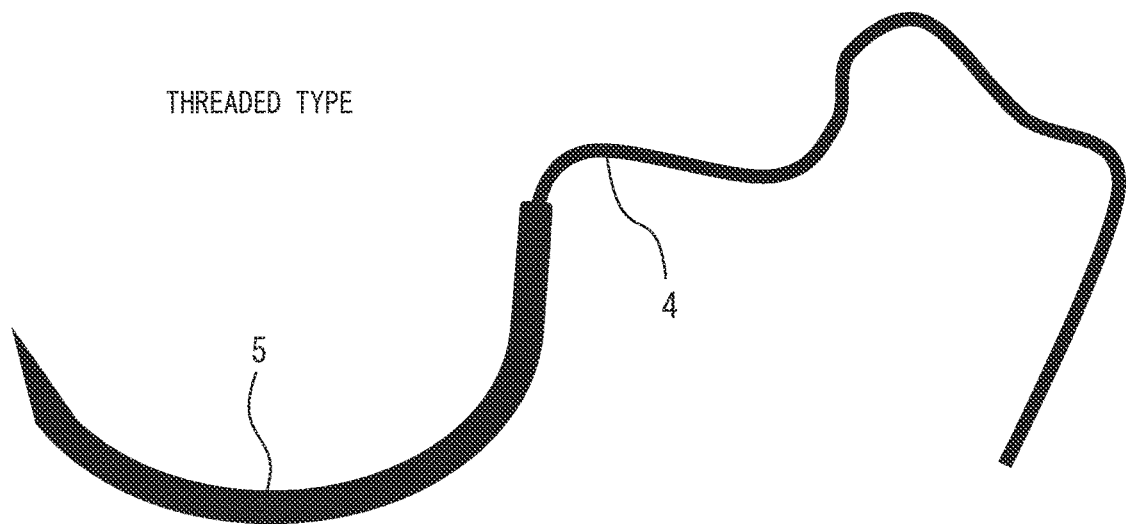

The shape of the suture thread fitting site (root) of the suture needle, for use in the suture of the stent and the graft includes: a normal eye type in which the suture thread is passed through the needle eye; a spring eye type having an incision that allows the suture thread to be pressed and mounted into the needle eye from the root; and a threaded type in which the needle root has a hollow portion, in which the suture thread is inserted and swaged to integrate the suture thread and the suture needle, as shown in FIG. 5. The production of the stent graft of the present embodiment may employ a suture needle having any of these root shapes. The spring eye type or the normal eye type may easily open needle holes because the inserted suture thread is folded at the suture thread fitting site into two parallelly arranged threads to increase the apparent thickness of the suture thread. Therefore, it is preferred to use a suture needle of threaded type having the suture thread integrated with the needle.

Figure 6:
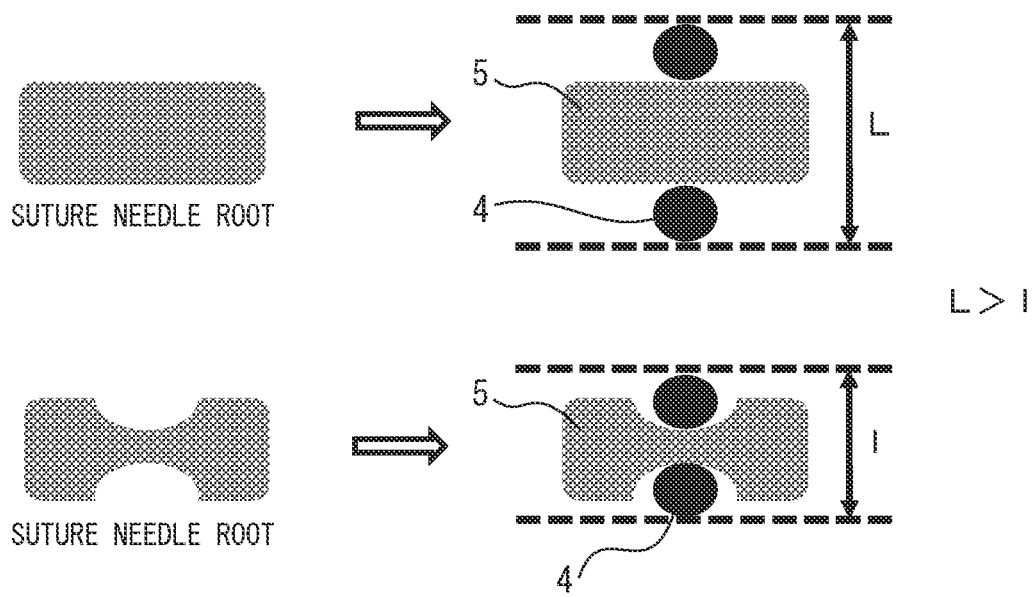
FIG. 6 is a diagram showing modified model of a suture needle root.
Figure 6:
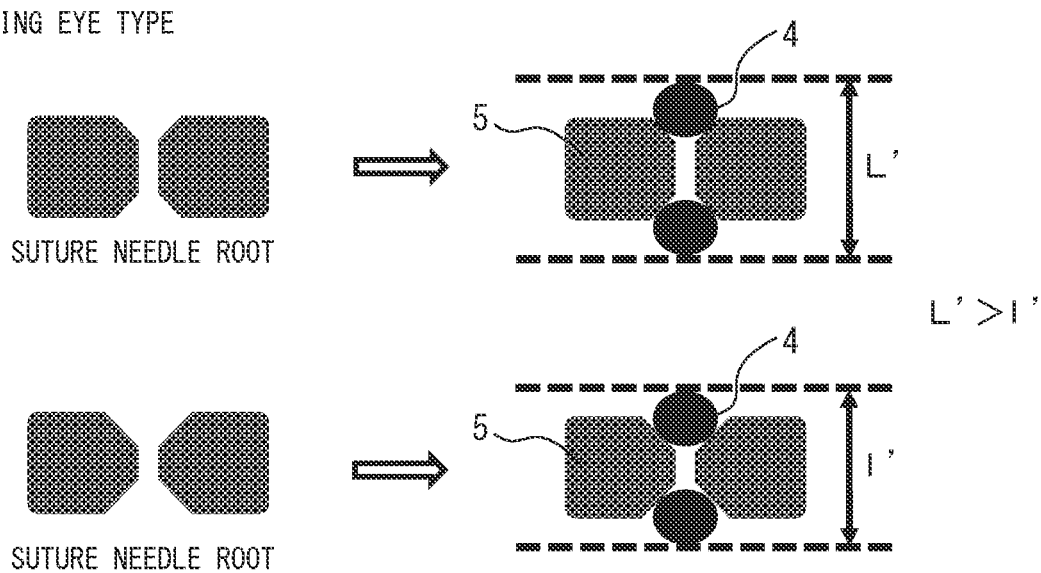
Figure 7:
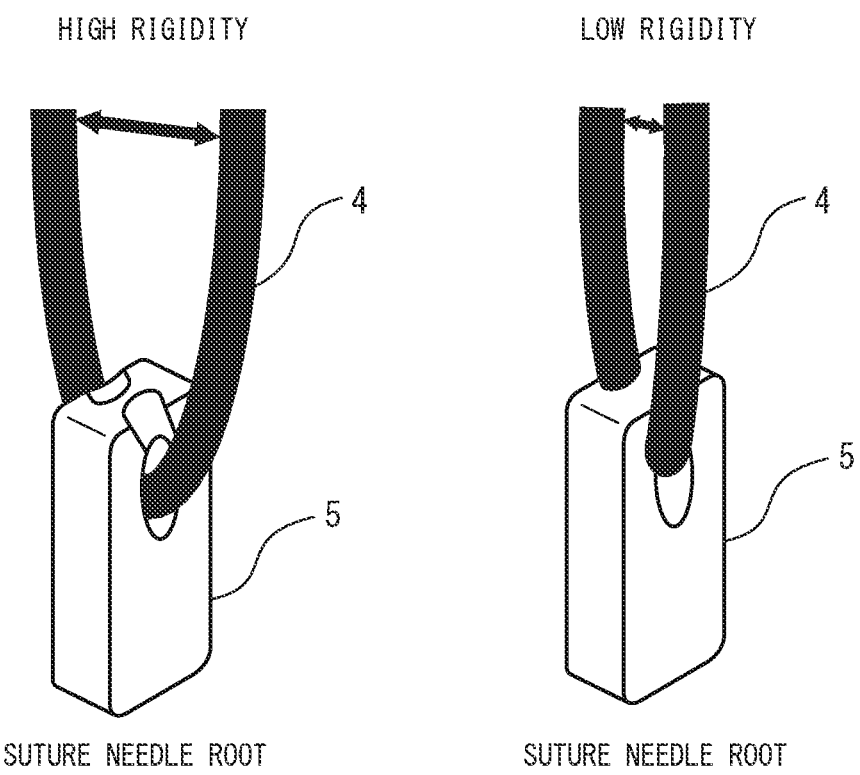
FIG. 7 is a diagram illustrating the effects of flexibility of a suture thread.

On the other hand, in the case of using a suture needle of threaded type, the suture needle must be replaced after consumption of a predetermined suture thread and may have a harmful effect on production cost or production efficiency. Therefore, a suture needle of spring eye type or normal eye type that permits arbitrary replacement of the suture thread may be preferred in some cases. In this case, as shown in FIG. 6, it is preferred to select a suture needle having concave notches or deeper concave notches at its root, because the total thickness of the two parallelly arranged suture threads can be decreased. In this context, use of the suture thread having a modulus of elasticity of 40 cN/dtex or less is effective for the case of using a suture needle of spring eye type or normal eye type. Specifically, a highly rigid suture thread cannot fit in the notches, as shown in FIG. 7, even if the suture needle has the concave notches at its root. Therefore, the total thickness of the two parallelly arranged suture threads cannot be decreased so that large needle holes are opened. By contrast, in the case of using the highly flexible suture thread having a modulus of elasticity of 40 cN/dtex or less, the two parallelly arranged suture threads are rendered neat and can fit in the notches at the root. Also, the suture thread having a braiding angle of 8° or larger and 30° or smaller and a braiding density (counts per unit length) of 12 counts/cm or higher and 45 counts/cm or lower is easily flattened with respect to stress in the cross sectional direction. Therefore, use of such a suture thread acts more effectively in the case of using a suture needle of spring eye type or normal eye type, because the total thickness of the two parallelly arranged suture thread is decreased.

The length of the suture needle or the curvature angle of the tip portion is not particularly limited and can be selected in light of easy suture and workability.

The joint location between the stent and the very thin graft and the number of joints can be selected according to the shape of the stent. Also, a conventional technique such as blanket stitching may be applied to the suture method.

The stent graft of the present embodiment is inserted into a catheter and delivered into a blood vessel. The stent graft of the present embodiment is as thin as a fabric thickness of 90 μm or smaller and is highly flexible. Therefore, the stent graft of the present embodiment can be inserted into a low profile catheter and consequently can be easily delivered into blood vessels with, low risk of damage to vascular walls. Any catheter of a conventional technique, such as tube type or balloon type, may be suitably used. Also, the stent graft inserted in a low profile catheter according to the present embodiment can be delivered into and indwelled in a blood vessel by use of a conventional delivery system.

The stent graft of the present embodiment allows a stent graft device to have a low profile, which can therefore reduce the physical and economical burdens on patients in such a way as to shorten the inpatient periods, and can also reduce risks such as vascular wall damage. Furthermore, the stent graft of the present invention can widen the range of applications even to cases that have hitherto been excluded as targets of stent grafting, such as females and Asians that have narrower arteries. In addition, the stent graft of the present invention minimizes needle holes at suture sites and neither enlarges needle holes during insertion in a catheter nor enlarges needle holes under a long-term beating environment. Therefore, the stent graft of the present invention can reduce the risk of type III endoleak.

EXAMPLES

Hereinafter, the present invention will be specifically described with reference to Examples. However, the present invention is not limited by these Examples. The main measurement values of physical properties were obtained by the following measurement methods.

(1) Thickness of Tubular Fabric (Graft)

The thickness of a graft was measured at four roughly equally spaced positions (arbitrarily selected depending on the diameter) in the circumferential direction of the graft by the method described below. This measurement was repeated three times in the length direction (10 cm to 30 cm), and the average of the 12 measurement values in total was calculated.

(Measurement Method)

The thickness is measured using a thickness gauge (PEACOCK Model G manufactured by Ozaki MFG. Co., Ltd.) after 10 seconds under pressure with a 1 N load.

(2) Modulus of Elasticity of Suture Thread

Figure 8:
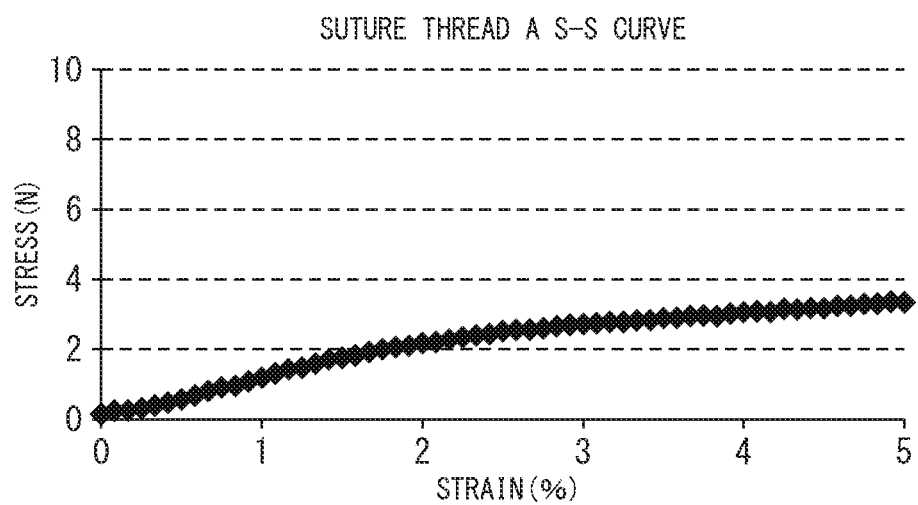
FIG. 8 is graphs showing S-S curves of suture thread A (upper) and suture thread B (lower).
Figure 8:
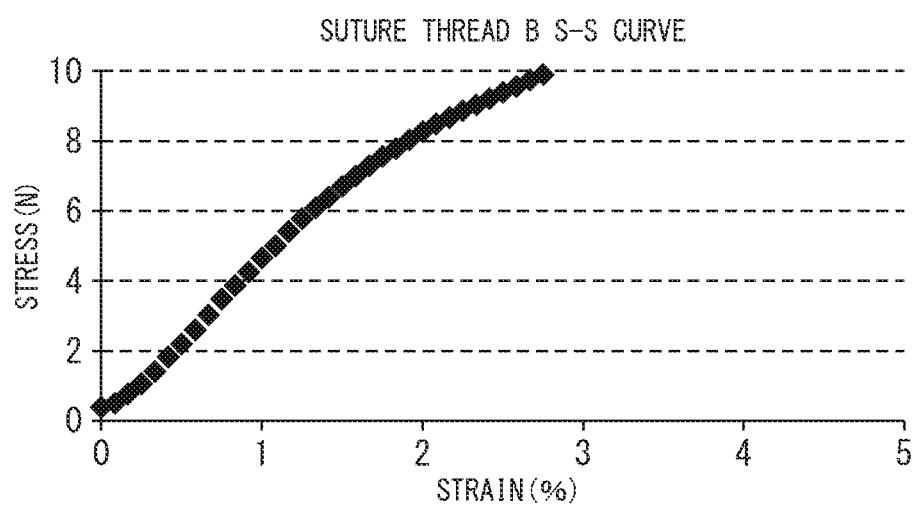

The modulus of elasticity of a suture thread is a tensile modulus of elasticity measured in a tensile tester TRAPEZIUM 2 (manufactured by Shimazu Corp.) according to JIS-L-1013, and was calculated from load for 1% tensile elongation and load for 2% elongation (see FIG. 8).

(3) Fiber Diameter of Suture Thread

To measure the fiber diameter of a suture thread, the suture thread was mounted onto an arbitrary stage without tension and observed under a microscope (digital microscope VHX-5000 manufactured by Keyence Corp.) at 200× magnification, and the diameter of the suture thread was determined using software included in the digital microscope. This operation was repeated five times in the length direction of the suture thread per m, and the calculated average was used as the fiber diameter of the suture thread.

(4) Measurement of Needle Hole Size Under 60 g Load

A suture needle (length: 14 mm, ½ circle) with a predetermined suture thread was used to insert the suture thread through a tubular graft mounted to a fixture with a width adjustable according to the diameter of the graft as shown in FIG. 1. Then, the suture thread was pulled with a load of 60 g in a direction of 90° with respect to the weft yarn. An opened needle hole was observed under a microscope (digital microscope VHX-5000 manufactured by Keyence Corp.) at 200× magnification and manually identified, and its area was determined using software included in the digital microscope. This operation was repeated five times, and the calculated average was used as the needle hole size.

(5) Measurement of the Number of Needle Holes and Needle Hole Size in Stent Graft A stent graft was observed on a structural unit basis in the circumferential direction under a microscope (digital microscope VHX-5000 manufactured by Keyence Corp.) at 200× magnification. Opened needle holes were manually identified. Their areas were determined, and the number of needle holes larger than 0.0025 mm$^2$ were measured. This operation was carried out on a structural unit basis in the length direction of the stent graft, and the average was used as the number of needle holes larger than 0.0025 mm$^2$ per structural unit.

(6) Water Permeability

The water permeability of the whole stent graft was measured according to ANSI/AAMI/ISO 7198:1998/2001.

(7) Prolonged Durability Test

The test was carried out using a vibratory loading acceleration tester at the number of vibrations of 90000000 according to ANSI/AAMI/ISO 7198:1998/2001.

Reference Examples 1 to 4 and Comparative Reference Example 1

The warp yarn and the weft yarn (both were polyester fibers) shown in Table 1 below were used in weaving using a shuttle loom and a Jacquard opening apparatus. The reed width and the number of warps were adjusted to attain a warp yarn cover factor of 800 or more. A plain weave tubular seamless woven fabric having an inner diameter of 50 mm and a length of 210 mm was prepared. This woven fabric was further finished by scouring and heat setting. All of the woven fabrics of these examples had a water permeability of 500 cc/min/cm$^2$ or less for the graft alone measured according to ANSI/AAMI/ISO 7198:1998/2001 and burst strength of 10 kg or more measured according to this specification, and were thus excellent in practical performance.

TABLE 1

| | Tubular seamless woven fabric (graft) | | | | | |
|---|---|---|---|---|---|---|
| | Warp yarn (dtex) Total fineness/single filament fineness | Weft yarn (dtex) Total fineness/single filament fineness | Warp yarn cover factor CFw | Weft Yarn cover factor CFf | Sum of warp yarn and weft yarn cover factors CFw + CFf | Thickness (μm) |
| Reference Example 1 | 39.4/1.64 | 30.3/0.10 | 1159 | 926 | 2085 | 69 |
| Reference Example 2 | 34.1/1.42 | 72.4/0.16 | 1212 | 896 | 2108 | 88 |
| Reference Example 3 | 34.1/1.42 | 20.1/0.13 | 1232 | 934 | 2166 | 60 |
| Reference Example 4 | 20.1/0.13 | 20.1/0.13 | 1004 | 950 | 1954 | 45 |
| Comparative Reference Example 1 | 76.1/2.53 | 39.4/1.64 | 1235 | 776 | 2011 | 121 |

Examples 1 to 8 and Comparative Examples 1 and 2

A suture needle (length: 17 mm, ½ circle) with the suture thread shown in Table 2 below was used to insert the suture thread through the tubular graft woven and after-treated in Reference Example 1. The suture thread was pulled with a load of 60 g, and the needle hole size was measured. The suture thread and the suture needle used were already sterilized with ethylene oxide. The results are shown in Table 2 below. As seen, in the case of using the suture thread having a modulus of elasticity of 40 cN/dtex or less, the needle hole size was equal to or smaller than 0.025 cm$^2$ serving as an index in all the examples. Thus, no large needle hole was opened even if a very thin graft was used. On the other hand, in Comparative Examples 1 and 2 using the suture thread having a modulus of elasticity exceeding 40 cN/dtex, large needle holes were opened and all exceeded 0.025 cm$^2$.

TABLE 2

| | Graft | Suture thread No. | Material | Physical properties of suture thread | | | | |
|---|---|---|---|---|---|---|---|---|
| | | | | Braiding angle (°) | Braiding density (counts/cm) | Fiber diameter (μm) | Modulus of elasticity (cN/dtex) | Needle hole size (mm$^2$) |
| Example 1 | Reference Example 1 (graft thickness: 66 μm) | Suture thread A | Polyester braid | 14 | 18 | 237 | 30.9 | 0.019 |
| Example 2 | | Suture thread B | Polyester braid | 17 | 27 | 275 | 37.0 | 0.016 |
| Example 3 | | Suture thread C | Polyester braid | 32 | 47 | 348 | 4.7 | 0.014 |
| Example 4 | | Suture thread D | Polyamide braid | 20 | 24 | 276 | 22.3 | 0.009 |
| Example 5 | | Suture thread E | Polyamide braid | 23 | 38 | 345 | 6.2 | 0.005 |
| Example 6 | | Suture thread F | Polyamide monofilament | — | — | 174 | 10.0 | 0.008 |
| Example 7 | | Suture thread G | Polyamide monofilament | — | — | 229 | 21.7 | 0.011 |
| Example 8 | | Suture thread H | Polyamide monofilament | — | — | 296 | 20.6 | 0.011 |
| Comparative Example 1 | | Suture thread I | Polyester braid | 4 | 11 | 158 | 48.0 | 0.038 |
| Comparative Example 2 | | Suture thread J | Polyester braid | 7 | 13 | 176 | 43.1 | 0.029 |

Examples 9 to 16 and Comparative Examples 3 and 4

The graft with a thickness of 60 μm prepared in Reference Example 3 was used to measure a needle hole size under a load of 60 g in the same way as in Examples 1 to 8 and Comparative Examples 1 and 2. As shown in Table 3 below, there is a tendency of needle hole enlargement due to the small graft thickness. However, as with the graft of Reference Example 1 (thickness: 66 μm), no large needle hole was opened by use of the suture thread having a modulus of elasticity of 40 cN/dtex or less even if a very thin graft was used. In Comparative Examples 3 and 4 using the suture thread having a modulus of elasticity exceeding 40 cN/dtex, all of needle holes exceeded 0.025 cm$^2$.

TABLE 3

| | Graft | Suture thread No. | Material | Physical properties of suture thread | | | | |
|---|---|---|---|---|---|---|---|---|
| | | | | Braiding angle (°) | Braiding density (counts/cm) | Fiber diameter (μm) | Modulus of elasticity (cN/dtex) | Needle hole size (mm$^2$) |
| Example 9 | Reference Example 3 (graft thickness: 60 μm) | Suture thread A | Polyester braid | 14 | 18 | 237 | 30.9 | 0.024 |
| Example 10 | | Suture thread B | Polyester braid | 17 | 27 | 275 | 37.0 | 0.019 |
| Example 11 | | Suture thread C | Polyester braid | 32 | 47 | 348 | 4.7 | 0.018 |

TABLE 3-continued

| | | | Physical properties of suture thread | | | | |
|---|---|---|---|---|---|---|---|
| Graft | Suture thread No. | Material | Braiding angle (°) | Braiding density (counts/cm) | Fiber diameter (μm) | Modulus of elasticity (cN/dtex) | Needle hole size (mm$^2$) |
| Example 12 | Suture thread D | Polyamide braid | 20 | 24 | 276 | 22.3 | 0.009 |
| Example 13 | Suture thread E | Polyamide braid | 23 | 38 | 345 | 6.2 | 0.006 |
| Example 14 | Suture thread F | Polyamide monofilament | — | — | 174 | 10.0 | 0.012 |
| Example 15 | Suture thread G | Polyamide monofilament | — | — | 229 | 21.7 | 0.016 |
| Example 16 | Suture thread H | Polyamide monofilament | — | — | 296 | 20.6 | 0.015 |
| Comparative Example 3 | Suture thread I | Polyester braid | 4 | 11 | 158 | 48.0 | 0.042 |
| Comparative Example 4 | Suture thread J | Polyester braid | 7 | 13 | 176 | 43.1 | 0.030 |

Examples 17 and 18

The grafts of Reference Examples 2 and 4 differing in thickness were used to measure a needle hole size under a load of 60 g under the conditions shown in Table 4 below. As a result, all of needle hole sizes were equal to or smaller than 0.025 mm$^2$.

TABLE 4

| | | | Physical properties of suture thread | | | | |
|---|---|---|---|---|---|---|---|
| Graft | | Suture thread No. | Material | Braiding angle (°) | Braiding density (counts/cm) | Fiber diameter (μm) | Modulus of elasticity (cN/dtex) | Needle hole size (mm$^2$) |
| Example 17 | Reference Example 2 (graft thickness: 88 μm) | Suture thread D | Polyamide braid | 20 | 24 | 276 | 22.3 | 0.009 |
| Example 18 | Reference Example 4 (graft thickness: 45 μm) | | | | | | | 0.020 |

Examples 19 to 22 and Comparative Examples 5 to 7

Eight W-shaped stent rings prepared with φ50 mm, the number of peaks of 4, the number of valleys of 4, and a height of 22 mm using a nitinol bar having a wire diameter of 0.5 mm were joined to the graft of Reference Example 1 (graft diameter: φ50 mm, length: 210 mm) by blanket stitching using the suture thread shown in Table 5 below. In this context, the suture needle used was a threaded suture needle (length: 14 mm, ½ circle) with each suture thread having a length of 1 m. The numbers of stitches at the peak section and the valley section were 4, the number of stitches per side was 12. The total number of stitches per structural unit was 160. The total number of stitches in the stent graft was 1280. The prepared stent graft was sterilized by an ordinary method using ethylene oxide gas.

Example 23

A suture thread composed of a polyester multifilament having a single filament fineness of 0.5 dtex and a total fineness of 75 dtex was attached to a suture needle (length: 17 mm, ½ circle) and sterilized with ethylene oxide gas. This suture thread was used to produce a stent graft in the same way as in Example 19. In the stent graft production, resistance upon penetration of the suture thread into the graft was smaller than that for suture thread B, which was also a polyester braid. Therefore, smaller holes were opened during suture. The integrity between the stent and the graft was also better than that obtained using suture thread B. All of the number of needle holes in the stent graft, the water permeability, and the like were favorable as shown in Table 6 below.

The number of needle holes larger than 0.025 mm$^2$ per structural unit of each stent graft prepared under the conditions described above was measured. By use of the suture thread having a modulus of elasticity of 40 cN/dtex or less, the number of large needle holes exceeding 0.025 mm$^2$ during the stent graft preparation was 10 or less per structural unit, as shown in Table 5 below, and was equivalent to that in the case of using Comparative Reference Example 1 (regular thickness graft). The water permeability in all of the examples was 300 cc/min/cm$^2$ or less and was thus favorable. On the other hand, in Comparative Examples 5 and 6 using the suture thread having a modulus of elasticity exceeding 40 cN/dtex, many needle holes larger than 0.025 mm$^2$ were opened, and the water permeability also exceeded 500 cc/min/cm$^2$.

Each of the stent grafts except for the ones of Comparative Examples 5 and 6 was further loaded in a vibratory loading acceleration tester and subjected to the prolonged durability test at the number of vibrations of 90000000. As a result, although a dozen of loosened or raveled sites of the suture thread were found in the stent graft of Example 19, favorable results were obtained in the other examples without any problem in the suture thread and notable needle hole enlargement after the durability test.

REFERENCE SIGNS LIST

1: Graft
2: Stent ring
3: Needle hole
4: Suture thread
5: Suture needle

TABLE 5

| Graft | Suture thread No. | Material | Braiding angle (°) | Braiding density (counts/cm) | Fiber diameter (μm) | Modulus of elasticity (cN/dtex) | Number of holes having needle hole size exceeding 0.025 mm² (no./structural unit) | Water permeability (cc/min/cm²) | Number of holes having needle hole size exceeding 0.025 mm² after prolonged durability test (no./structural unit) |
|---|---|---|---|---|---|---|---|---|---|
| Ex. 19 | Ref. Ex. 1 (graft thickness: 66 μm) | Suture thread B | Polyester braid | 17 | 28 | 278 | 36.4 | 6 | 167 | 8 |
| Ex. 20 | | Suture thread C | Polyester braid | 32 | 47 | 349 | 4.7 | 4 | 116 | 8 |
| Ex. 21 | | Suture thread D | Polyamide braid | 22 | 25 | 281 | 21.7 | 5 | 121 | 6 |
| Ex. 22 | | Suture thread E | Polyamide braid | 23 | 38 | 346 | 6.3 | 3 | 105 | 3 |
| Comp. Ex. 5 | | Suture thread I | Polyester braid | 5 | 11 | 158 | 47.8 | 18 | 680 | (not carried out) |
| Comp. Ex. 6 | | Suture thread J | Polyester braid | 7 | 13 | 177 | 42.9 | 13 | 572 | (not carried out) |
| Comp. Ex. 7 | Comp. Ref. Ex. 1 (graft thickness: 121 μm) | Suture thread D | Polyamide braid | 20 | 25 | 279 | 22.2 | 3 | 191 | 4 |

TABLE 6

| Graft | Suture thread No. | Material | Braiding angle (°) | Braiding density (counts/cm) | Fiber diameter (μm) | Modulus of elasticity (cN/dtex) | Number of holes having needle hole size exceeding 0.025 mm² (no./structural unit) | Water permeability (cc/min/cm²) | Number of holes having needle hole size exceeding 0.025 mm² after prolonged durability test (no./structural unit) |
|---|---|---|---|---|---|---|---|---|---|
| Ex. 23 | Ref. Ex. 1 (graft thickness: 66 μm) | Suture thread K | Polyester braid | 20 | 34 | 281 | 28.1 | 3 | 124 | 4 |

The stent graft of the present invention allows a stent graft device to have a low profile, which can therefore reduce the physical and economical burdens on patients in such a way as to shorten the inpatient periods, and can also reduce risks such as vascular wall damage. Furthermore, the stent graft of the present invention can widen the range of applications even to cases that have hitherto been excluded as targets of stent grafting treatment, such as females and Asians that have narrower arteries. In addition, the stent graft of the present invention minimizes needle holes at suture sites and neither enlarges needle holes during insertion in a catheter nor enlarges needle holes under a long-term beating environment. Therefore, the stent graft of the present invention can reduce the risk of type III endoleak.

The invention claimed is:

1. A stent graft comprising a proximal end, a distal end, and a lumen disposed between the proximal end and the distal end, wherein the stent graft comprises a tubular graft, a stent, and a suture thread, the tubular graft is a woven fabric having a thickness of 10 μm or larger and 90 μm or smaller, wherein the suture thread joins together the tubular graft and the stent and wherein the suture thread has a modulus of elasticity of 40 cN/dtex or less and is in a braid form in which three or more fiber bundles (yarns) each comprising a plurality of filaments are interlaced, and the braid has a braiding angle of 8° or larger and 30° or smaller and a braiding density of 12 counts/cm or higher and 45 counts/cm or lower.

2. The stent graft according to claim 1, wherein the suture thread has a fiber diameter of 350 μm or smaller.

3. The stent graft according to claim 2, wherein the suture thread is a multifilament made of at least one selected from the group consisting of polyester, polyamide, polyolefin, polytetrafluoroethylene, and silk.

4. The stent graft according to claim 2, wherein the graft is a woven fabric composed of multifilaments made of at least one selected from the group consisting of polyester, polyamide, polyolefin, polytetrafluoroethylene, and silk.

5. The stent graft according to claim 1, wherein the suture thread is a multifilament made of at least one selected from the group consisting of polyester, polyamide, polyolefin, polytetrafluoroethylene, and silk.

6. The stent graft according to claim 5, wherein the graft is a woven fabric composed of multifilaments made of at least one selected from the group consisting of polyester, polyamide, polyolefin, polytetrafluoroethylene, and silk.

7. The stent graft according to claim 1, wherein the fiber bundles are textured yarns having a porosity of 4 to 70%.

8. The stent graft according to claim 7, wherein the fiber bundles are made of polyester and have a total fineness of 30 dtex or more and 200 dtex or less and a single filament fineness of 1.0 dtex or less.

9. The stent graft according to claim 7, wherein the graft is a woven fabric composed of multifilaments made of at least one selected from the group consisting of polyester, polyamide, polyolefin, polytetrafluoroethylene, and silk.

10. The stent graft according to claim 1, wherein the fiber bundles are made of polyester and have a total fineness of 30 dtex or more and 200 dtex or less and a single filament fineness of 1.0 dtex or less.

11. The stent graft according to claim 10, wherein the graft is a woven fabric composed of multifilaments made of at least one selected from the group consisting of polyester, polyamide, polyolefin, polytetrafluoroethylene, and silk.

12. The stent graft according to claim 1, wherein the graft is a woven fabric composed of multifilaments made of at least one selected from the group consisting of polyester, polyamide, polyolefin, polytetrafluoroethylene, and silk.

13. The stent graft according to claim 12, wherein the graft is a woven fabric composed of polyester.

14. The stent graft according to claim 12, wherein the graft is a seamless woven fabric composed of a polyester fiber containing 90 wt % or more of polyethylene terephthalate with respect to the graft weight, and the polyester fiber has a total fineness of 7 dtex or more and 120 dtex or less and a single filament fineness of 1.0 dtex or less.

15. The stent graft according to claim 1, wherein when the suture thread is inserted through the graft and is pulled with a load of 60 g, a needle hole area in the graft is 0.025 mm² or smaller.

16. A stent graft device comprising the stent graft according to claim 1.

17. The stent graft according to claim 1, wherein the stent graft comprises a plurality of suture threads.

18. The stent graft according to claim 17, wherein the plurality of suture threads have the modulus of elasticity of 40 cN/dtex or less and are in the braid form in which three or more fiber bundles (yarns) each comprising the plurality of filaments are interlaced, and the braid has the braiding angle of 8° or larger and 30° or smaller and the braiding density of 12 counts/cm or higher and 45 counts/cm or lower.

19. The stent graft according to claim 1, wherein the modulus of elasticity is 1 cN/dtex or more and 35 cN/dtex and less.

20. The stent graft according to claim 19, wherein the modulus of elasticity is 2 cN/dtex or more and 30 cN/dtex and less.

21. The stent graft according to claim 1, wherein the suture thread has an elongation percentage of 0.2% or more and 2.0% or less.

22. The stent graft according to claim 21, wherein the elongation percentage is 0.3% or more and 1.8% or less.

23. The stent graft according to claim 22, wherein the elongation percentage is 0.4% or more and 1.5% or less.

* * * * *